US012393655B2

(12) United States Patent
Kato

(10) Patent No.: US 12,393,655 B2
(45) Date of Patent: Aug. 19, 2025

(54) AUTHENTICATION DEVICE

(71) Applicants: KABUSHIKI KAISHA TOSHIBA, Tokyo (JP); Toshiba Infrastructure Systems & Solutions Corporation, Kawasaki Kanagawa (JP)

(72) Inventor: Masakazu Kato, Tokyo (JP)

(73) Assignees: Kabushiki Kaisha Toshiba, Tokyo (JP); Toshiba Infrastructure Systems & Solutions Corporation, Kawasaki (JP)

( * ) Notice: Subject to any disclaimer, the term of this patent is extended or adjusted under 35 U.S.C. 154(b) by 360 days.

(21) Appl. No.: 18/067,915

(22) Filed: Dec. 19, 2022

(65) Prior Publication Data

US 2023/0120591 A1    Apr. 20, 2023

Related U.S. Application Data

(63) Continuation of application No. PCT/JP2021/026651, filed on Jul. 15, 2021.

(30) Foreign Application Priority Data

Jul. 21, 2020   (JP) ................................. 2020-124443

(51) Int. Cl.
*G06F 21/32* (2013.01)
*G06F 1/16* (2006.01)
*G06V 40/12* (2022.01)

(52) U.S. Cl.
CPC .............. *G06F 21/32* (2013.01); *G06F 1/163* (2013.01); *G06V 40/1365* (2022.01)

(58) Field of Classification Search
None
See application file for complete search history.

(56) References Cited

U.S. PATENT DOCUMENTS

| 7,849,619 B2 | 12/2010 | Mosher, Jr. et al. |
| 2003/0177370 A1 | 9/2003 | Smith |

(Continued)

FOREIGN PATENT DOCUMENTS

| JP | 2005-71225 A | 3/2005 |
| JP | 2005-301448 A | 10/2005 |

(Continued)

OTHER PUBLICATIONS

European Patent Office, Extended European Search Report in EP App. No. 21846637.3, 7 pages (Jun. 10, 2024).

(Continued)

*Primary Examiner* — Cai Y Chen
(74) *Attorney, Agent, or Firm* — Finnegan, Henderson, Farabow, Garrett & Dunner, LLP

(57) ABSTRACT

According to an embodiment, an authentication device for authenticating a user includes a biological sensor, a storage unit, a communication interface, a detection mechanism, and a processor. The biological sensor acquires biological information. The detection mechanism detects attachment/detachment. The processor authenticates a user using the biological information, and when the authentication is successful, the processor then stores authentication information in the storage unit and turns off the authentication device. When the communication interface receives a magnetic field from an external device, the processor activates the authentication device using power from the communication interface, and upon receipt of an authentication command, if the storage unit stores the authentication information, the processor transmits an authentication signal indicating that authentication is successful to the external device. When the detection mechanism detects that the authentication device is removed from the user, the processor deletes the authentication information in the storage unit.

8 Claims, 10 Drawing Sheets

(56) References Cited

U.S. PATENT DOCUMENTS

| | | | |
|---|---|---|---|
| 2005/0071647 A1 | 3/2005 | Fujinuma et al. | |
| 2015/0161371 A1* | 6/2015 | Hoshi | G06F 21/445 726/19 |
| 2016/0013872 A1* | 1/2016 | Åstrand | H04W 12/068 455/41.2 |
| 2020/0019682 A1 | 1/2020 | Lee et al. | |
| 2022/0100841 A1 | 3/2022 | Yang et al. | |

FOREIGN PATENT DOCUMENTS

| | | |
|---|---|---|
| JP | 2006-506694 A | 2/2006 |
| JP | 4140822 | 8/2008 |
| JP | 2016-71598 A | 5/2016 |
| JP | 2017-531235 A | 10/2017 |
| WO | WO 2014/147713 A1 | 9/2014 |
| WO | WO 2015/011552 A1 | 1/2015 |
| WO | WO 2018/048563 A1 | 3/2018 |

OTHER PUBLICATIONS

Japan Patent Office, International Search Report in International Application No. PCT/JP2021/026651, 2 pages (Sep. 7, 2021).
Intellectual Property Office of Singapore, Notice for Eligibility of Grant in SG App. No. 11202261339W, 5 pages (May 26, 2025).

\* cited by examiner

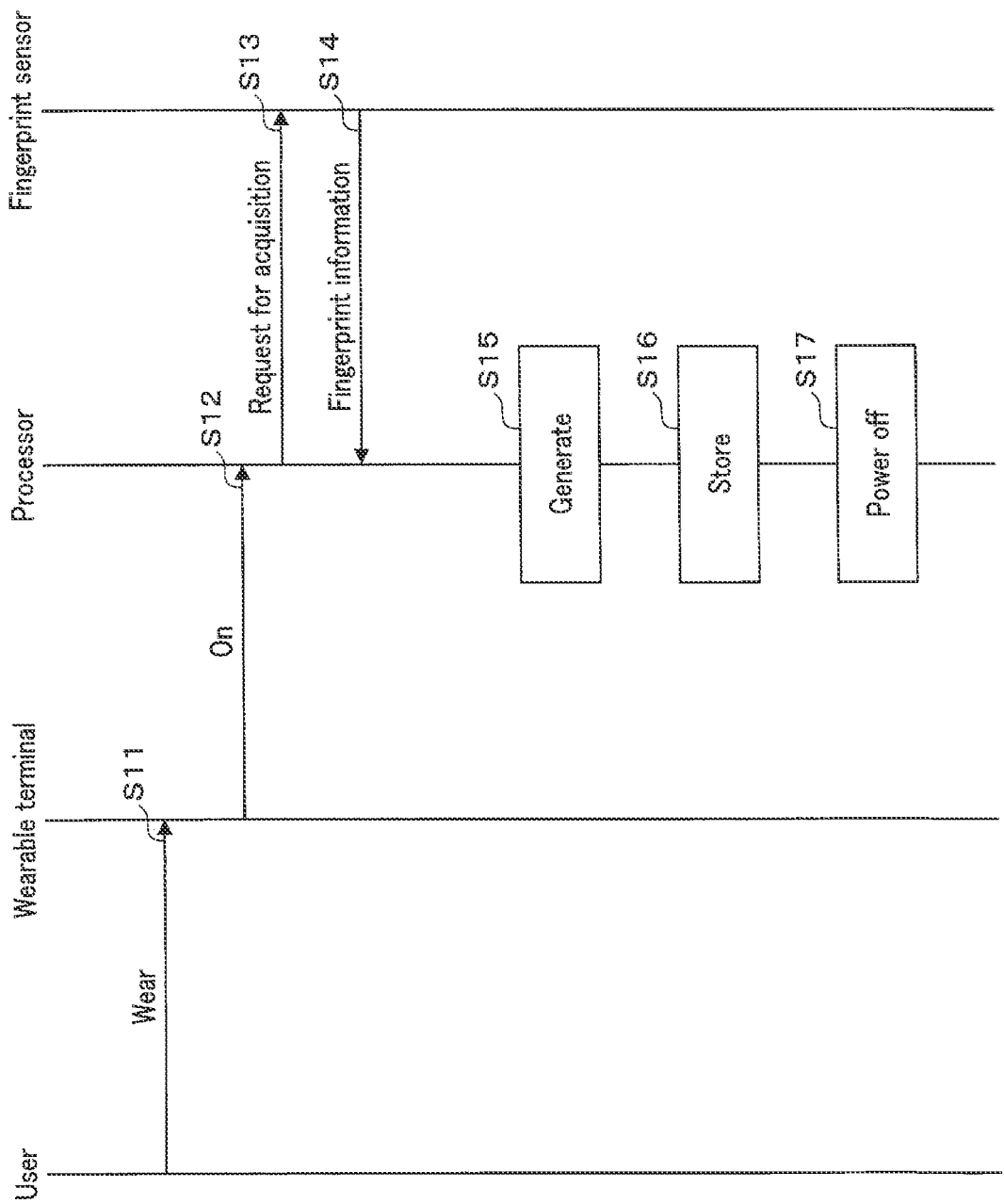
F I G. 5

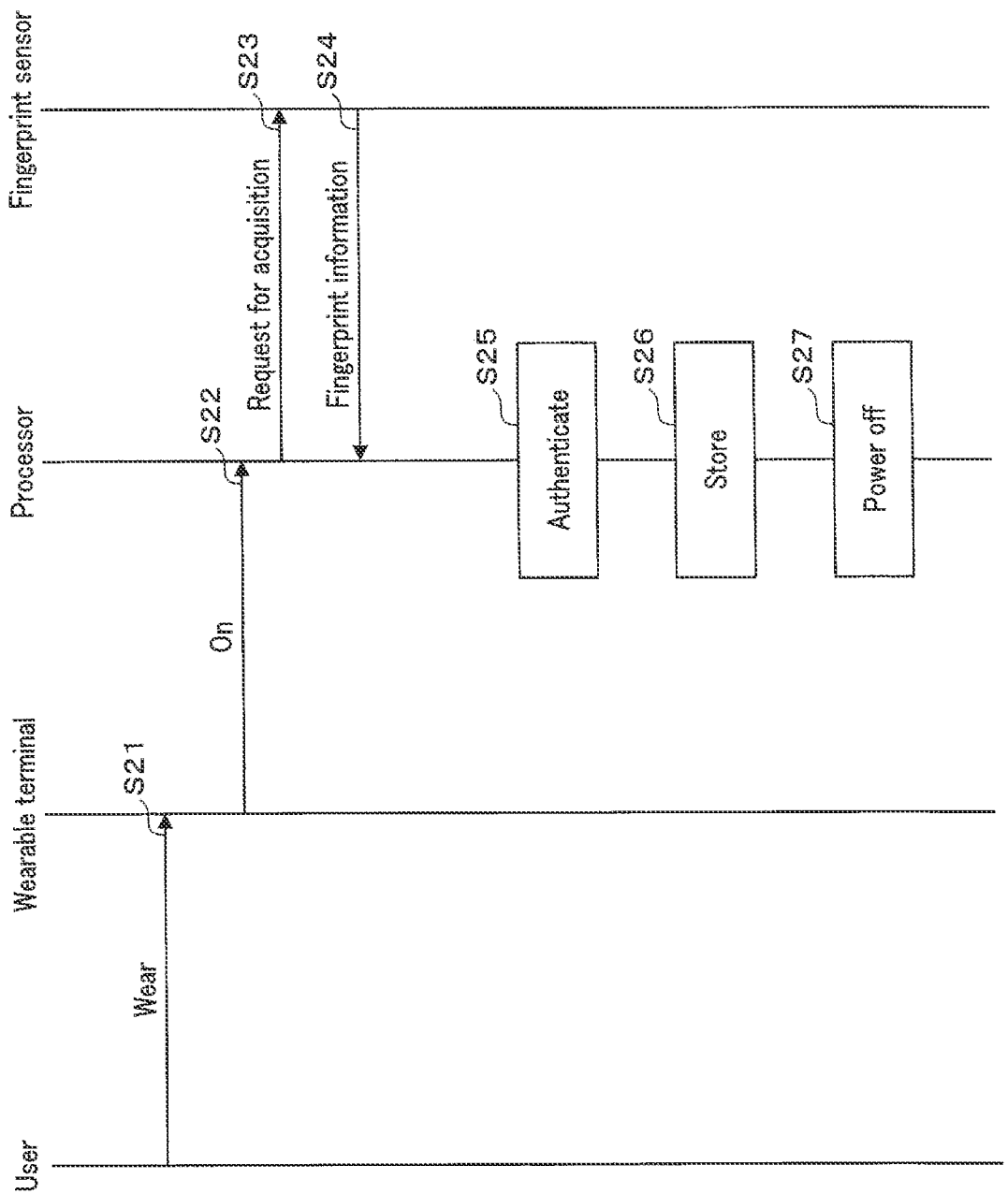
F I G. 6

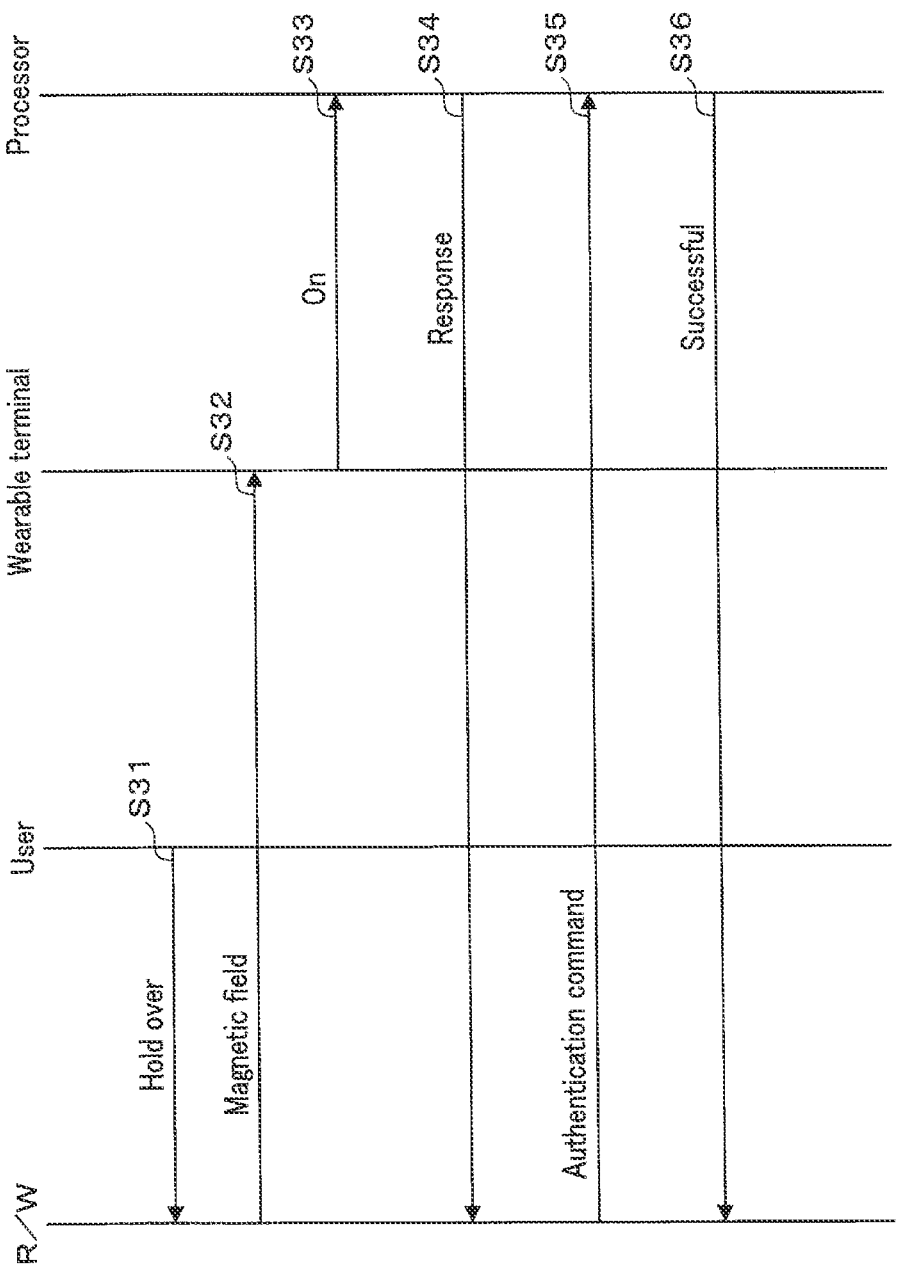
F I G. 7

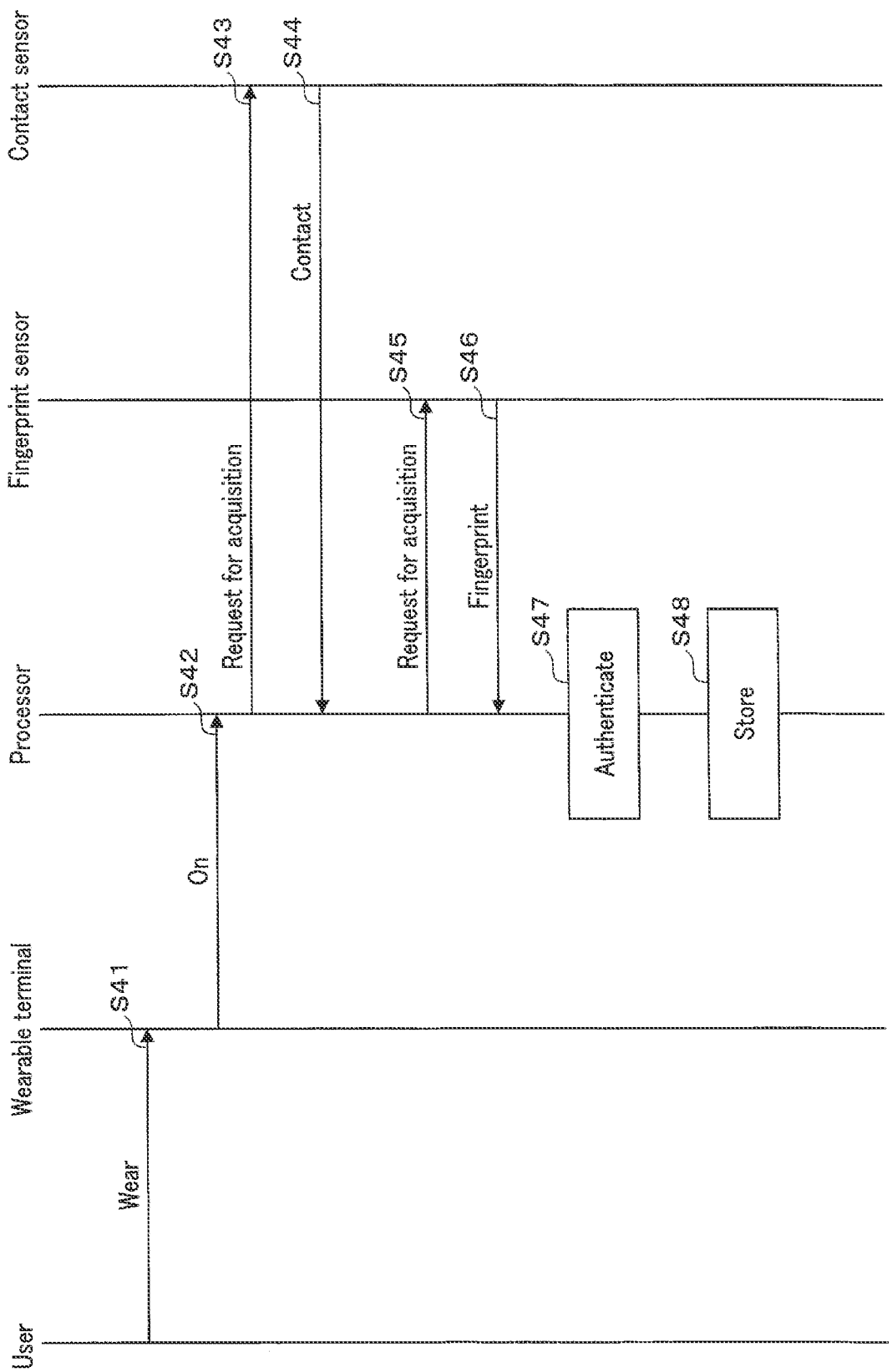
F I G. 11

AUTHENTICATION DEVICE

CROSS REFERENCE TO RELATED APPLICATIONS

This application is a Continuation application of PCT Application No. PCT/JP2021/026651, filed Jul. 15, 2021 and based upon and claiming the benefit of priority from Japanese Patent Application No. 2020-124443, filed Jul. 21, 2020, the entire contents of all of which are incorporated herein by reference.

FIELD

Embodiments described herein relate generally to an authentication device.

BACKGROUND

Wearable terminals have been provided that connect wirelessly to devices such as smartphones, doors, or PCs to unlock the devices. Such wearable terminals use fingerprints or the like to authenticate a user and unlock the device.

Conventionally, a wearable terminal needs to authenticate a user by using a fingerprint or the like each time the device is unlocked.

CITATION LIST

Patent Literature

Patent Literature 1: International Publication No. 2014/147713

SUMMARY

Technical Problem

To solve the problem described above, an authentication device capable of effectively authenticating a user is provided.

Solution to Problem

According to an embodiment, an authentication device for authenticating a user includes a biological sensor, a storage unit, a communication interface, a detection mechanism, and a processor. The biological sensor acquires biological information. The storage unit stores authentication information. The communication interface transmits and receives data to and from an external device. The detection mechanism detects attachment/detachment of the authentication device. The processor authenticates a user using the biological information acquired by the biological sensor, and when the authentication of the user is successful, the processor then stores the authentication information in the storage unit and turns off the authentication device. When the communication interface receives a magnetic field from the external device, the processor activates the authentication device using power from the communication interface, and upon receipt of an authentication command through the communication interface, if the storage unit stores the authentication information, the processor transmits an authentication signal indicating that authentication is successful to the external device through the communication interface. When the detection mechanism detects that the authentication device is removed from the user, the processor deletes the authentication information in the storage unit.

BRIEF DESCRIPTION OF DRAWINGS

FIG. 5 is a sequence diagram showing an operation example of the authentication system according to the first embodiment.

FIG. 6 is a sequence diagram showing an operation example of the authentication system according to the first embodiment.

FIG. 7 is a sequence diagram showing an operation example of the authentication system according to the first embodiment.

FIG. 11 is a sequence diagram showing an operation example of an authentication system according to the second embodiment.

DETAILED DESCRIPTION

Hereinafter, embodiments will be described with reference to the drawings.

First Embodiment

First, a first embodiment is described.

An authentication system according to the embodiment includes a wearable terminal carried by a predetermined user and a reader/writer. When the wearable terminal and the reader/writer come close to each other within a predetermined distance, communication is established between them. The wearable terminal transmits an authentication signal indicating that the authentication is successful to the reader/writer and unlocks the device.

Figure 1:
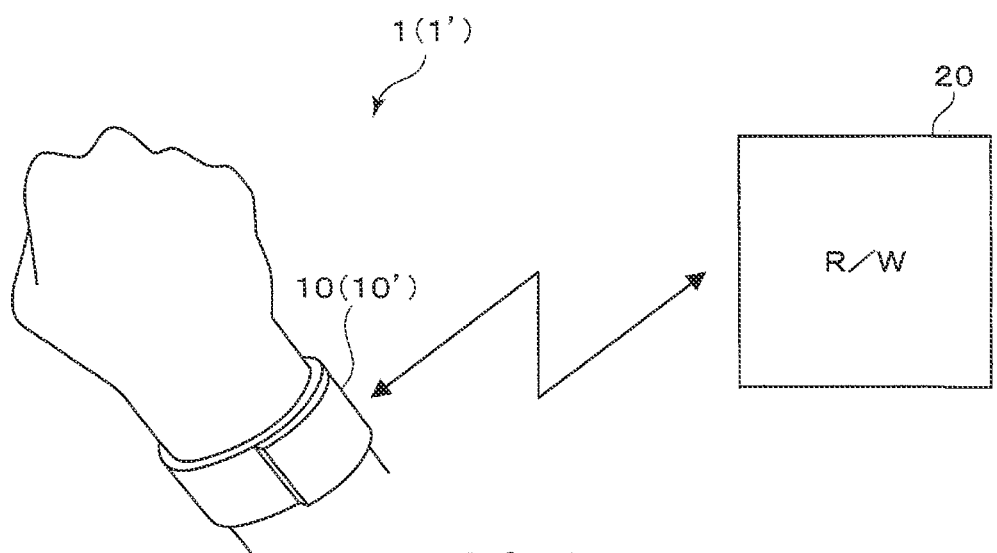
FIG. 1 is a diagram showing a configuration example of an authentication system according to a first embodiment.

FIG. 1 shows a configuration example of an authentication system 1 according to the embodiment. As shown in FIG. 1, the authentication system 1 includes a wearable terminal 10 and a reader/writer 20. The wearable terminal 10 and the reader/writer 20 are communicably connected to each other.

The wearable terminal 10 (authentication device) is a terminal carried by a user. When the wearable terminal 10 approaches the reader/writer 20 at a distance at which communication therebetween is possible, the wearable terminal 10 establishes communication with the reader/writer 20. The wearable terminal 10 may be paired with the reader/writer 20 in advance. Here, the wearable terminal 10 is a wristwatch-type terminal. The wearable terminal 10 will be described in detail later.

The reader/writer 20 (external device) is an interface device for transmitting and receiving data to and from the wearable terminal 10 in a non-contact manner.

The reader/writer 20 includes an antenna, a communication control unit, and the like for wirelessly communicating with the wearable terminal 10. The reader/writer 20 performs power supply, clock supply, reset control, data transmission and reception, and the like with respect to the wearable terminal 10.

With such functions, the reader/writer 20 performs power supply to the wearable terminal 10, activation (start) of the wearable terminal 10, clock supply, reset control, transmission of various commands, reception of responses to the transmitted commands, and the like.

When the communication with the wearable terminal 10 is established, the reader/writer 20 transmits a command for authenticating the user. The reader/writer 20 receives a response indicating an authentication result of the user as a response to the command. The reader/writer 20 transmits the response to the device connected to itself.

If the response indicates that the authentication is successful, the device unlocks. For example, the device is a smartphone, a door, a PC, or the like. Note that the device and the reader/writer 20 may be integrally formed.

Next, the wearable terminal 10 is described.

Figure 2:
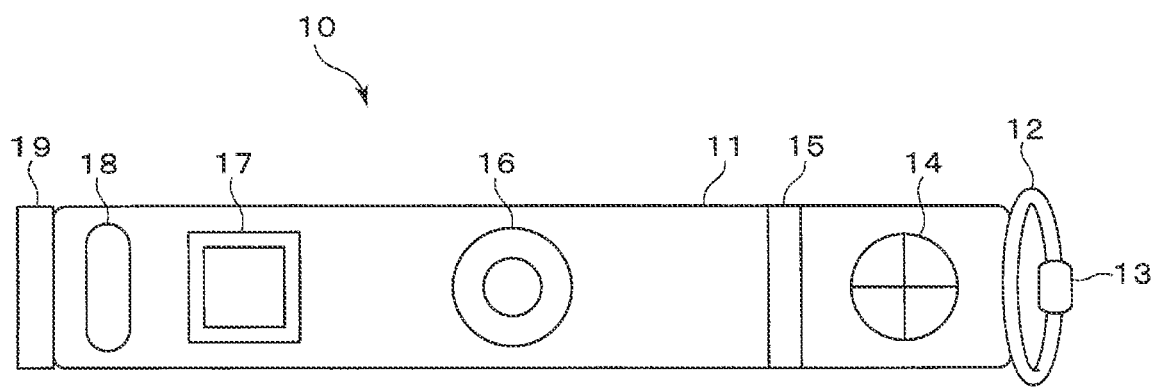
FIG. 2 is a diagram schematically showing a configuration example of a wearable terminal according to the first embodiment.

FIG. 2 shows an outer appearance of the wearable terminal 10. As shown in FIG. 2, the wearable terminal 10 includes a band 11, an attachment mechanism 12, a switch 13, an antenna 14, a detachment mechanism 15, a battery 16, a fingerprint sensor 17, a display mechanism 18, a detachment mechanism 19, and the like.

The band 11 forms an outer shape of the wearable terminal 10. The band 11 is formed in a belt shape having a predetermined length. The band 11 is wound around the arm of the user. For example, the band 11 is made of rubber, silicon, leather, or the like.

An attachment mechanism 12 is provided at one end of the band 11. The attachment mechanism 12 is a member used by the user to fasten the band 11 to the wrist. The attachment mechanism 12 is a ring-shaped member having a size that allows the detachment mechanism 19 to be inserted. The attachment mechanism 12 fastens the wearable terminal 10 to the wrist of the user by inserting the detachment mechanism 19 into the attachment mechanism 12.

A switch 13 is provided inside the attachment mechanism 12. The switch 13 is pressed when the detachment mechanism 19 passes the attachment mechanism 12. In other words, the switch 13 is pressed when the user wears or removes the wearable terminal 10. The switch 13 functions as a detection mechanism that detects attachment/detachment of the wearable terminal 10.

The switch 13 may be a toggle switch. Further, the switch 13 may be turned on by being in contact with the detachment mechanism 19.

The antenna 14 (communication interface) is an antenna for transmitting and receiving data to and from the reader/writer 20. Further, the antenna 14 functions as a power source for supplying electric power through radio waves from the reader/writer 20.

For example, the antenna 14 supports a Bluetooth (registered trademark) connection or a near field communication (NFC) connection.

The detachment mechanism 15 is formed at a position close to the attachment mechanism 12 in the band 11. The detachment mechanism 15 is a member for attaching and detaching the wearable terminal 10. The detachment mechanism 15 is detachable from the detachment mechanism 19. The detachment mechanism 15 fastens the wearable terminal 10 to the wrist of the user by fastening the detachment mechanism 19 that has passed through the attachment mechanism 12.

The battery 16 supplies electric power to each unit of the wearable terminal 10. The battery 16 may be a secondary battery that can be externally charged. For example, the battery 16 is charged by electric power from the antenna 14. Further, the battery 16 may be a disposable battery.

The fingerprint sensor 17 (biological sensor) is provided near the other end of the band 11 opposite to the attachment mechanism 12. The fingerprint sensor 17 is installed on the inner side (the side in contact with the wrist of the user) of the band 11.

The fingerprint sensor 17 acquires a fingerprint (fingerprint image) from any one of the user's fingers. The fingerprint sensor 17 transmits fingerprint information indicating the fingerprint acquired from the finger to the processor 111 (described later). The fingerprint information may be a fingerprint image. The fingerprint information may be a feature amount of a fingerprint image or the like.

For example, the fingerprint sensor 17 is constituted by an optical sensor for photographing a fingerprint and other components. Alternatively, the fingerprint sensor 17 may be constituted by a sensor that detects electrostatic capacity and other components.

The display mechanism 18 displays information to the user based on control from the processor 111. For example, the display mechanism 18 is constituted by a lamp such as an LED (Light Emitting Diode). Alternatively, the display mechanism 18 may be constituted by a liquid crystal monitor.

The detachment mechanism 19 is provided at the other end of the band 11 opposite to the attachment mechanism 12. The detachment mechanism 19 is a member for attaching and detaching the wearable terminal 10. The detachment mechanism 19 is detachable from the detachment mechanism 15. As described above, the detachment mechanism 19 fastens the wearable terminal 10 to the wrist of the user by fastening the detachment mechanism 19 to the detachment mechanism 15 in a state in which the detachment mechanism 19 passes through the attachment mechanism 12.

Note that the switch 13 may be provided in the detachment mechanism 19.

Figure 3:
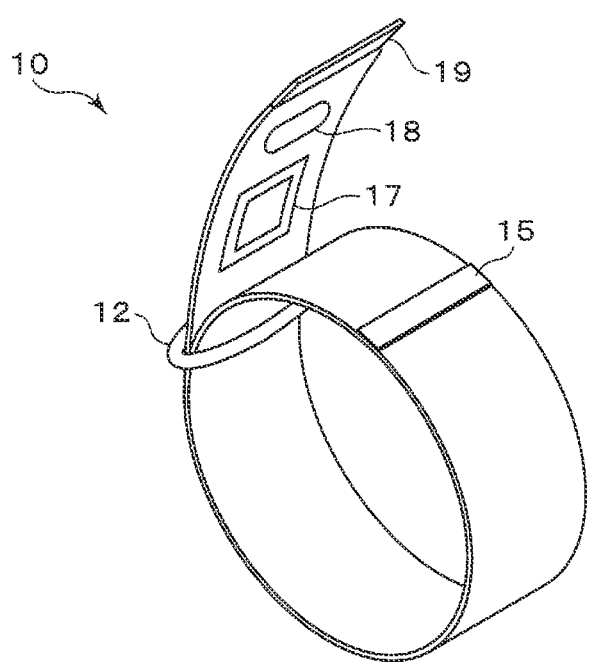
FIG. 3 is a diagram showing an example of wearing the wearable terminal according to the first embodiment.

FIG. 3 shows a state in which the wearable terminal 10 is worn on the wrist of the user. As shown in FIG. 3, the user inserts the detachment mechanism 19 into the attachment mechanism 12 in a state where the band 11 is wound around the wrist. When the detachment mechanism 19 is inserted into the attachment mechanism 12, the fingerprint sensor 17 and the display mechanism 18 face the user. The user wears the wearable terminal 10 on their own wrist by fastening the detachment mechanism 19 to the detachment mechanism 15.

Next, a control system of the wearable terminal 10 is described.

Figure 4:
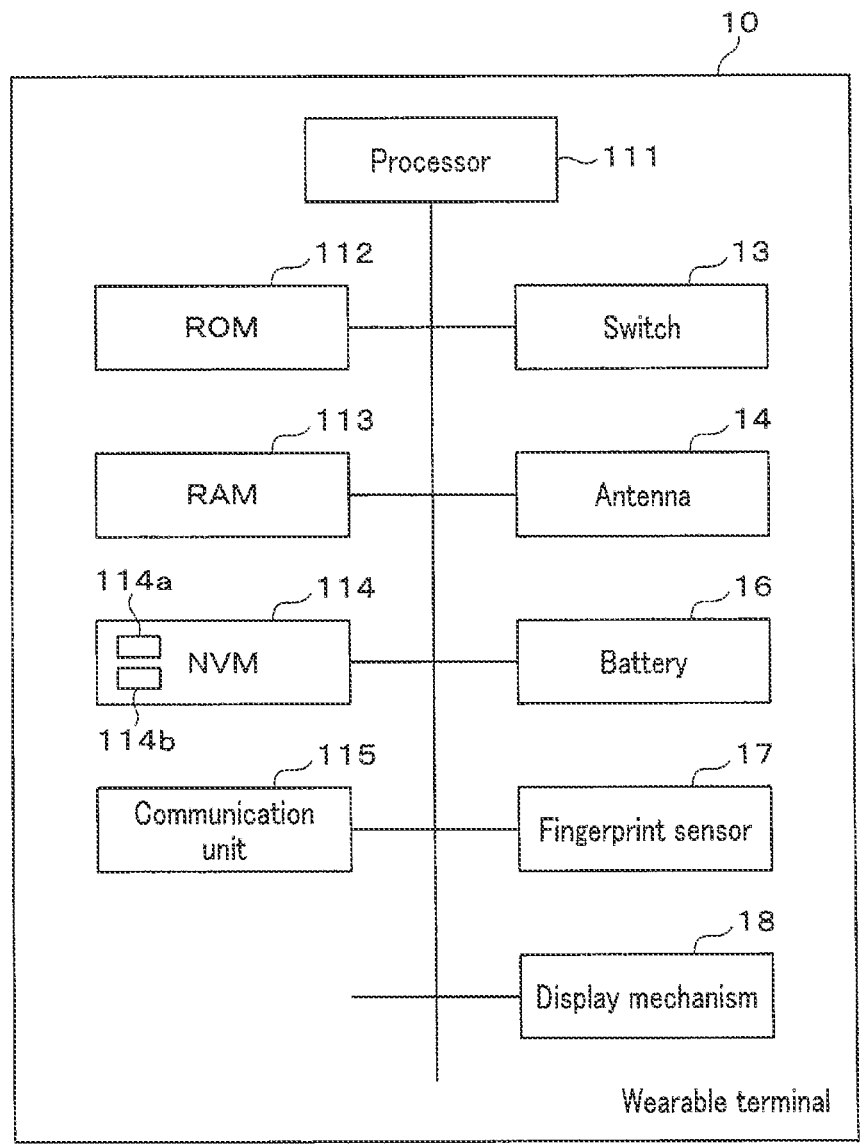
FIG. 4 is a block diagram showing a configuration example of the wearable terminal according to the first embodiment.

FIG. 4 is a block diagram showing a control system of the wearable terminal 10. As shown in FIG. 4, the wearable terminal 10 includes a processor 111, a ROM 112, a RAM 113, an NVM 114, a communication unit 115, a switch 13, an antenna 14, a battery 16, a fingerprint sensor 17, a display mechanism 18, and the like.

The processor 111, the ROM 112, the RAM 113, the NVM 114, the communication unit 115, the switch 13, the antenna 14, the battery 16, the fingerprint sensor 17, and the display mechanism 18 are connected to each other via a databus or the like.

The switch 13, the antenna 14, the battery 16, the fingerprint sensor 17, and the display mechanism 18 are as described above.

The processor 111 has a function of controlling the overall operation of the wearable terminal 10. The processor 111 may include an internal cache, various interfaces, and the like. The processor 111 realizes various processes by executing programs stored in advance in an internal memory, the ROM 112, or the NVM 114.

Some of the various functions realized by the processor 111 executing the program may be realized by a hardware circuit. In this case, the processor 111 controls the functions performed by the hardware circuit.

The ROM 112 is a non-volatile memory in which a control program, control data, and the like are stored in advance. The control program and the control data stored in the ROM 112 are pre-loaded according to the specifications of the wearable terminal 10.

The RAM 113 is a volatile memory. The RAM 113 temporarily stores information that is being processed by the processor 111. The RAM 113 stores various application programs based on an instruction from the processor 111. The RAM 113 may store information necessary for executing the application programs, results of running the application programs, and the like.

The NVM 114 (storage unit) is a data-writable and rewritable nonvolatile memory. The NVM 114 includes, for example, a hard disk drive (HDD), a solid state drive (SDD), a flash memory, or the like. The NVM 114 stores control programs, applications, various kinds of information, and the like in accordance with the operational use of the wearable terminal 10.

The NVM 114 includes a storage area 114a for storing a template for authenticating a user, a storage area 114b for storing authentication information indicating that authentication is successful, and the like.

The template is a template corresponding to the fingerprint information acquired by the fingerprint sensor 17. Herein, the template is a template for performing fingerprint authentication. For example, the template includes a fingerprint image of the user, a characteristic amount of the fingerprint image, a network for fingerprint authentication, or the like.

The authentication information indicates that the processor 111 has succeeded in fingerprint authentication. For example, the authentication information may be a flag or the like. For example, the storage area 114b stores "1" as the authentication information.

The communication unit 115 is an interface that transmits and receives data to and from an external device. For example, the communication unit 115 may support wired or wireless LAN (Local Area Network) connection.

The wearable terminal 10 may include other configurations as needed in addition to the configuration illustrated in FIGS. 3 and 4, or a specific configuration may be excluded from the wearable terminal 10.

Next, the functions implemented by the wearable terminal 10 are described. The functions implemented by the processor 111 are implemented by the processor 111 executing a program stored in an internal memory, the ROM 112, the NVM 114, or the like.

First, the processor 111 has a function of registering a template.

Herein, assume that the user winds the band 11 of the wearable terminal 10 around the wrist and inserts the detachment mechanism 19 into the attachment mechanism 12. That is, the user brings the wearable terminal 10 into the state illustrated in FIG. 3.

When the detachment mechanism 19 passes through the attachment mechanism 12, the switch 13 is pressed. When the switch 13 is pressed, the processor 111 activates the wearable terminal 10 by using power from the battery 16. When the wearable terminal 10 is activated, the processor 111 determines whether or not the storage area 114a stores a template.

When it is determined that the storage area 114a does not store the template, the processor 111 registers a template.

The processor 111 causes the fingerprint sensor 17 to acquire fingerprint information. Here, the user brings a finger into contact with the fingerprint sensor 17.

The processor 111 acquires fingerprint information from the fingerprint sensor 17. Upon obtaining the fingerprint information, the processor 111 generates a template from the obtained fingerprint information in accordance with a predetermined algorithm. When the template is generated, the processor 111 stores the generated template in the storage area 114a.

Further, the processor 111 has a function of storing authentication information upon successful fingerprint authentication using the fingerprint sensor 17.

Herein, assume that the user winds the band 11 of the wearable terminal 10 around the wrist and inserts the detachment mechanism 19 into the attachment mechanism 12. That is, the user brings the wearable terminal 10 into the state illustrated in FIG. 3. Assume that the storage area 114a stores a template. Also assume that the storage area 114b does not store authentication information.

When the detachment mechanism 19 passes through the attachment mechanism 12, the switch 13 is pressed. When the switch 13 is pressed, the processor 111 activates the wearable terminal 10 by using power from the battery 16. When the wearable terminal 10 is activated, the processor 111 determines whether or not the storage area 114a stores a template.

When it is determined that the storage area 114a stores the template, the processor 111 determines whether the storage area 114b stores the authentication information. When it is determined that the storage area 114b does not store the authentication information, the processor 111 performs fingerprint authentication.

The processor 111 causes the fingerprint sensor 17 to acquire fingerprint information. Here, the user brings a finger into contact with the fingerprint sensor 17.

After acquiring the fingerprint information, the processor 111 compares the template stored in the storage area 114a with the acquired fingerprint information according to a predetermined algorithm. When the template and the fingerprint information match (are identified), the processor 111 determines that the fingerprint authentication is successful.

When it is determined that the fingerprint authentication is successful, the processor 111 stores the authentication information in the storage area 114b. The processor 111 may display information indicating that the fingerprint authentication is successful on the display mechanism 18.

When the authentication information is stored in the storage area 114b, the processor 111 turns off the wearable terminal 10. As will be described later, the processor 111 shifts to a state in which it can be activated by the magnetic field from the reader/writer 20.

If the template and the fingerprint information do not match, the processor 111 determines that the fingerprint authentication has failed. Upon determining that the fingerprint authentication has failed, the processor 111 ends the operation. The processor 111 may display information indicating that the fingerprint authentication has failed on the display mechanism 18.

The processor 111 has a function of transmitting an authentication signal indicating that authentication is successful to the reader/writer 20 while the storage area 114*b* stores the authentication information.

Here, assume that the user holds the wearable terminal 10 over the communication range of the reader/writer 20. Assume that the reader/writer 20 outputs a magnetic field.

The antenna 14 receives a magnetic field from the reader/writer 20. Upon receipt of the magnetic field, the antenna 14 provides power generated by the magnetic field. When the antenna 14 starts supplying power, the processor 111 activates the wearable terminal 10 by using the power from the antenna 14.

Here, assume that the reader/writer 20 transmits an authentication command for authenticating the user to the wearable terminal 10.

The processor 111 receives the authentication command through the antenna 14. Upon receipt of the authentication command, the processor 111 determines whether or not the storage area 114*b* stores authentication information.

When it is determined that the authentication information is stored in the storage area 114*b*, the processor 111 transmits a response (authentication signal) indicating that the authentication is successful to the reader/writer 20 through the antenna 14. The authentication signal may store an ID of the wearable terminal or the like.

The processor 111 may receive, from the reader/writer 20 via the antenna 14, a command for requesting IDs (IDs of the wearable terminals 10) stored in the NVM 114 of the wearable terminals 10. When the authentication information is stored in the storage area 114*b*, the processor 111 transmits a response including the ID to the reader/writer 20 through the antenna 14.

When it is determined that the authentication information is not stored in the storage area 114*b*, the processor 111 transmits a response indicating that the authentication has failed to the reader/writer 20 through the antenna 14.

The processor 111 has a function of deleting the authentication information when the wearable terminal 10 is removed from the wrist of the user.

Here, the user removes the wearable terminal 10 from their wrist. That is, the user detaches the detachment mechanism 19 from the detachment mechanism 15. In addition, the user pulls out the detachment mechanism 19 from the attachment mechanism 12.

Assume that the storage area 114*a* stores a template. In addition, assume that the storage area 114*b* stores authentication information.

When the detachment mechanism 19 passes through the attachment mechanism 12, the switch 13 is pressed. That is, the switch 13 detects that the wearable terminal 10 has been removed from the user. When the switch 13 is pressed, the processor 111 activates the wearable terminal 10 by using power from the battery 16. When the wearable terminal 10 is activated, the processor 111 determines whether or not the storage area 114*a* stores a template.

When it is determined that the storage area 114*a* stores the template, the processor 111 determines whether the storage area 114*b* stores the authentication information. When it is determined that the storage area 114*b* stores the authentication information, the processor 111 deletes the authentication information in the storage area 114*b*.

The processor 111 may delete the authentication information in the storage area 114*b* when it detects that the detachment mechanism 19 is detached from the detachment mechanism 15 by using a sensor or the like.

Next, an operation example of the authentication system 1 is described.

First, an operation example in which the authentication system 1 registers a template is described.

FIG. 5 is a sequence diagram for explaining an operation example in which the authentication system 1 registers a template.

Here, assume that the storage area 114*a* does not store a template.

First, the user wears the wearable terminal 10 (S11). In this step, the user brings the wearable terminal 10 into the state shown in FIG. 3.

When the user wears the wearable terminal 10, the switch 13 of the wearable terminal 10 is pressed (S12). When the switch 13 is pressed, the processor 111 activates the wearable terminal 10 by using power from the battery 16.

When the wearable terminal 10 is activated, the processor 111 causes the fingerprint sensor 17 to acquire fingerprint information (S13). In this step, the user brings their finger into contact with the fingerprint sensor 17. The fingerprint sensor 17 transmits the fingerprint information acquired from the user's finger to the processor 111 (S14).

The processor 111 acquires fingerprint information of the user from the fingerprint sensor 17. Upon obtaining the fingerprint information, the processor 111 generates a template based on the obtained fingerprint information (S15).

When the template is generated, the processor 111 stores the generated template in the storage area 114*a* (S16). When the generated template is stored in the storage area 114*a*, the processor 111 turns off the wearable terminal 10 (S17).

When the processor 111 turns off the wearable terminal 10, the authentication system 1 ends the operation.

Next, an operation example in which the authentication system 1 stores authentication information is described.

FIG. 6 is a sequence diagram for explaining an operation example in which the authentication system 1 stores authentication information.

Here, assume that the storage area 114*a* stores a template. Also assume that the storage area 114*b* does not store authentication information.

First, the user wears the wearable terminal 10 (S21). In this step, the user brings the wearable terminal 10 into the state shown in FIG. 3.

When the user wears the wearable terminal 10, the switch 13 of the wearable terminal 10 is pressed (S22). When the switch 13 is pressed, the processor 111 activates the wearable terminal 10 by using power from the battery 16.

When the wearable terminal 10 is activated, the processor 111 causes the fingerprint sensor 17 to acquire fingerprint information (S23). In this step, the user brings their finger into contact with the fingerprint sensor 17. The fingerprint sensor 17 transmits the fingerprint information acquired from the user's finger to the processor 111 (S24).

The processor 111 acquires fingerprint information of the user from the fingerprint sensor 17. When the fingerprint information is acquired, the processor 111 performs fingerprint authentication by comparing the template with the acquired fingerprint information (S25). Here, assume that the processor 111 has succeeded in the fingerprint authentication.

When the fingerprint authentication is performed, the processor 111 stores the authentication information in the storage area 114b (S26). When the authentication information is stored in the storage area 114b, the processor 111 turns off the wearable terminal 10 (S27).

When the processor 111 turns off the wearable terminal 10, the authentication system 1 ends the operation.

When the processor 111 fails in the fingerprint authentication, the authentication system 1 ends the operation.

Next, an operation example in which the authentication system 1 authenticates a user is described.

FIG. 7 is a sequence diagram for explaining an operation example in which the authentication system 1 authenticates a user.

Here, assume that the user wears the wearable terminal 10 on their own wrist. In addition, assume that the storage area 114b stores authentication information.

The user holds the wearable terminal 10 over the reader/writer 20 (S31). When the user holds the wearable terminal 10 over the reader/writer 20, the reader/writer 20 outputs a magnetic field to the wearable terminal 10 (S32). The reader/writer 20 may continue to output the magnetic field.

When the reader/writer 20 outputs a magnetic field, the antenna 14 supplies power (S33). When the antenna 14 starts supplying power, the processor 111 activates the wearable terminal 10 by using the power from the antenna 14.

When the wearable terminal 10 is activated, the processor 111 transmits an initial response to the reader/writer 20 through the antenna 14 (S34). The reader/writer 20 receives the initial response from the wearable terminal 10.

Upon receipt of the initial response, the reader/writer 20 transmits an authentication command to the wearable terminal 10 (S35). The processor 111 of the wearable terminal 10 receives the authentication command through the antenna 14.

When the authentication command is received, the processor 111 transmits a response indicating that the authentication is successful to the reader/writer 20 through the antenna 14 (S36). The reader/writer 20 receives the response from the wearable terminal 10.

When the reader/writer 20 receives the response, the authentication system 1 ends the operation.

When the storage area 114b does not store the authentication information, the processor 111 transmits a response indicating that the authentication has failed in response to the authentication command.

Next, an operation example in which the authentication system 1 deletes authentication information is described.

Figure 8:
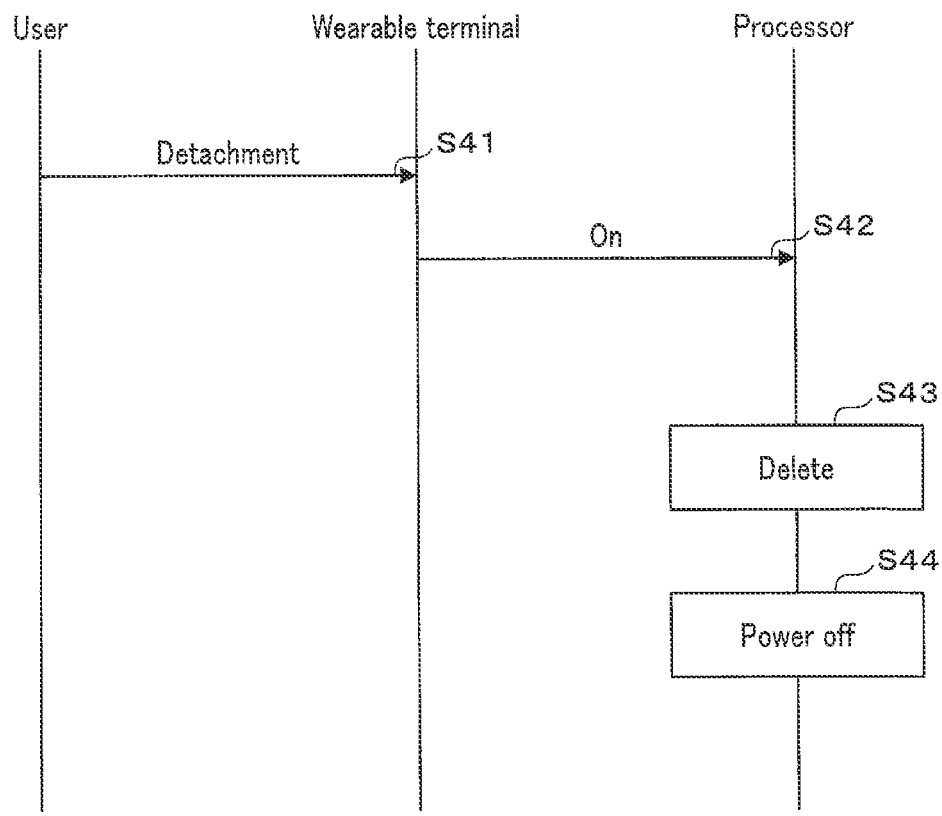
FIG. 8 is a sequence diagram showing an operation example of the authentication system according to the first embodiment.

FIG. 8 is a sequence diagram for explaining an operation example in which the authentication system 1 deletes authentication information.

Here, assume that the storage area 114a stores a template. In addition, assume that the storage area 114b stores authentication information.

The user removes the wearable terminal 10 from their wrist (S41). That is, the user pulls out the detachment mechanism 19 from the attachment mechanism 12. When the detachment mechanism 19 is pulled out from the attachment mechanism 12, the switch 13 is pressed (S42). When the switch 13 is pressed, the processor 111 activates the wearable terminal 10 by using power from the battery 16.

When the wearable terminal 10 is activated, the processor 111 deletes the authentication information in the storage area 114b (S43). When the authentication information is deleted, the processor 111 turns off the wearable terminal 10 (S44).

When the processor 111 turns off the wearable terminal 10, the authentication system 1 ends the operation.

Note that the switch 13 may be provided in the detachment mechanism 19. In this case, the switch 13 is pressed when the detachment mechanism 19 passes through the attachment mechanism 12.

Further, the switch 13 may be installed inside the band 11. In this case, the switch 13 is pressed when the band 11 is wound around the wrist of the user.

In addition, the switch 13 may be pressed when the user wears or removes the wearable terminal 10.

When the supply of power from the antenna 14 and the pressing of the switch 13 conflict, the processor 111 may activate the wearable terminal 10 by using the power of the battery 16.

The wearable terminal 10 may include a micro processing unit (MPU) for performing fingerprint authentication. In this case, the processor 111 transmits the fingerprint information acquired by the fingerprint sensor 17 to the MPU. The MPU performs fingerprint authentication based on the fingerprint information from the fingerprint sensor 17, and transmits the result of the fingerprint authentication to the processor 111. For example, the MPU is a secure element (SE) or the like.

The processor 111 may authenticate the user using biological information other than the fingerprint. In this case, the wearable terminal includes a biological sensor. For example, the biological information is a face image, a vein, an iris, a voiceprint, handwriting, or the like. The biological information is not limited to a specific configuration.

The wearable terminal configured as described above authenticates a user at the time of being worn and stores authentication information. The wearable terminal is turned off, with the authentication information being stored therein. When activated by a magnetic field from the reader/writer, the wearable terminal transmits an authentication signal to the reader/writer. As a result, the wearable terminal can transmit the authentication signal to the reader/writer without authenticating the user each time the device is unlocked. In addition, the wearable terminal can reduce power consumption by being turned off after storing the authentication information.

Further, the wearable terminal deletes the authentication information at the time of removal. As a result, the wearable terminal is prevented from being handed over to another person while in a state of holding the authentication information. It is thus possible to prevent the wearable terminal from being illegally used by another person and the device being unlocked.

Second Embodiment

Next, a second embodiment is described.

The authentication system according to the second embodiment is different from the authentication system according to the first embodiment in that authentication information is deleted when the wearable terminal 10 detects that the user has been separated from the wearable terminal 10 by using a contact sensor. Thus, detailed description of the other components to which the same reference numerals are given is omitted.

FIG. 1 illustrates a configuration example of an authentication system 1' according to the second embodiment. As shown in FIG. 1, the authentication system 1' includes a wearable terminal 10' and a reader/writer 20. The wearable terminal 10' and the reader/writer 20 are communicably connected to each other.

Figure 9:
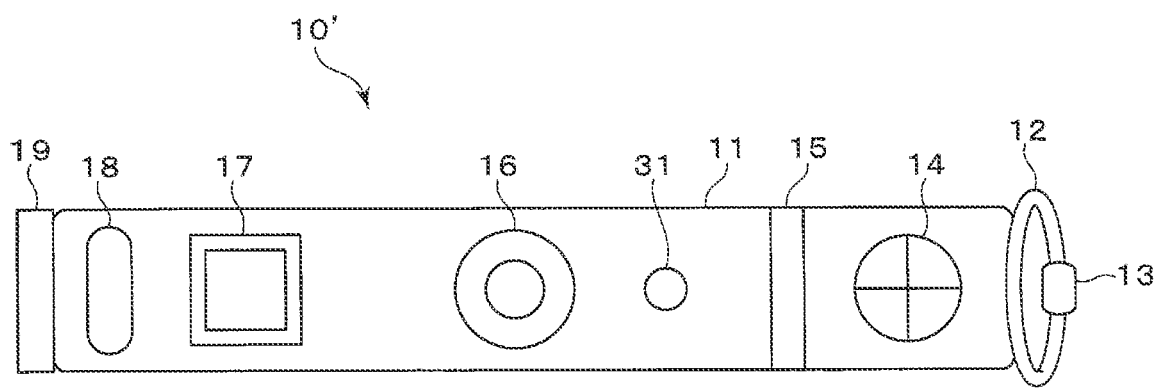
FIG. 9 is a diagram schematically showing a configuration example of a wearable terminal according to a second embodiment.

FIG. 9 shows an appearance of the wearable terminal 10'. As shown in FIG. 2, the wearable terminal 10 includes a band 11, an attachment mechanism 12, a switch 13, an antenna 14, a detachment mechanism 15, a battery 16, a fingerprint sensor 17, a display mechanism 18, a detachment mechanism 19, a contact sensor 31, and the like.

The contact sensor 31 detects that the wearable terminal 10' is worn by the user. In other words, the contact sensor 31 detects contact between the wearable terminal 10' and the user.

The contact sensor 31 transmits a sensor signal indicating contact (or non-contact) with the user to the processor 111. The contact sensor 31 may transmit a parameter for determining a presence or absence of contact to the processor 111.

For example, the contact sensor 31 is a sensor that detects a vital sign (body temperature, pulse, or the like) of the user. The contact sensor 31 may be a sensor that detects contact with the user (or the skin of the user), such as an ultrasonic sensor, an optical sensor (such as an infrared sensor), a pressure sensor, or an energization sensor. The configuration of the contact sensor 31 is not limited to a specific configuration.

Figure 10:
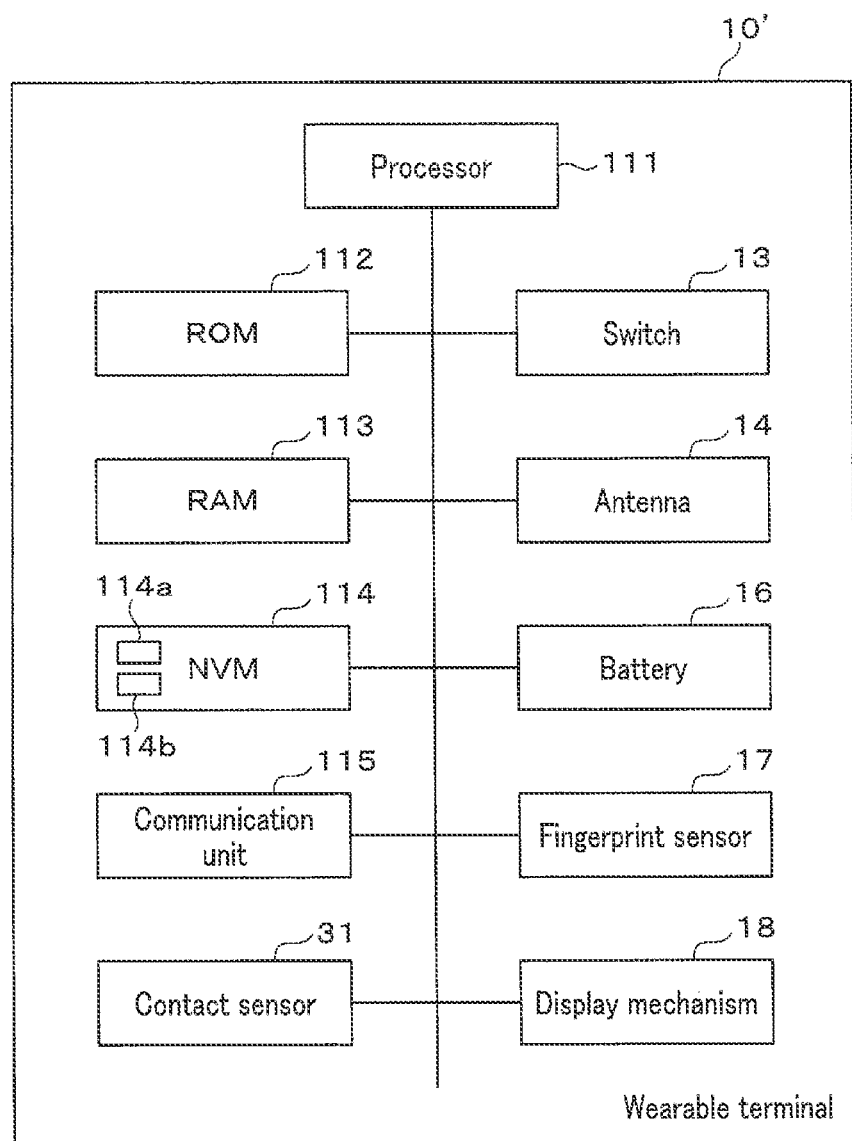
FIG. 10 is a block diagram showing a configuration example of the wearable terminal according to the second embodiment.

FIG. 10 is a block diagram showing a control system of the wearable terminal 10'. As shown in FIG. 10, the wearable terminal 10 includes a processor 111, a ROM 112, a RAM 113, an NVM 114, a communication unit 115, a switch 13, an antenna 14, a battery 16, a fingerprint sensor 17, a display mechanism 18, a contact sensor 31, and the like.

The processor 111, the ROM 112, the RAM 113, the NVM 114, the communication unit 115, the switch 13, the antenna 14, the battery 16, the fingerprint sensor 17, the display mechanism 18, and the contact sensor 31 are connected to each other via a databus or the like.

The wearable terminal 10' may include a configuration as needed in addition to the configuration illustrated in FIGS. 9 and 10, or a specific configuration may be excluded from the wearable terminal 10'.

Next, the functions implemented by the wearable terminal 10' are described. The functions implemented by the processor 111 are implemented by the processor 111 executing a program stored in an internal memory, the ROM 112, the NVM 114, or the like.

The wearable terminal 10' implements the following functions in addition to the functions implemented by the wearable terminal 10.

The processor 111 has a function of performing fingerprint authentication, with the user being in contact with the wearable terminal 10.

Herein, assume that the user winds the band 11 of the wearable terminal 10 around the wrist and inserts the detachment mechanism 19 into the attachment mechanism 12. That is, the user brings the wearable terminal 10 into the state illustrated in FIG. 3. Assume that the storage area 114a stores a template. Also assume that the storage area 114b does not store authentication information.

When the detachment mechanism 19 passes through the attachment mechanism 12, the switch 13 is pressed. When the switch 13 is pressed, the processor 111 activates the wearable terminal 10 by using power from the battery 16. When the wearable terminal 10 is activated, the processor 111 determines whether or not the storage area 114a stores a template.

When it is determined that the storage area 114a stores the template, the processor 111 determines whether the storage area 114b stores the authentication information. When it is determined that the storage area 114b does not store the authentication information, the processor 111 causes the contact sensor 31 to detect contact with the user.

The contact sensor 31 transmits a sensor signal indicating contact (or non-contact) with the user to the processor 111. Herein, the contact sensor 31 transmits a sensor signal indicating contact with the user to the processor 111.

The processor 111 receives a sensor signal indicating contact with the user from the contact sensor 31. Upon receipt of the sensor signal, the processor 111 performs fingerprint authentication. The fingerprint authentication and the operation after the fingerprint authentication are the same as those in the first embodiment, and a description thereof is omitted.

The processor 111 also has a function of deleting the authentication information when the user is separated from the wearable terminal 10.

Herein, assume that the storage area 114b stores authentication information.

The processor 111 determines whether the user has been separated from the contact sensor 31 based on the sensor signal from the contact sensor 31. In other words, the processor 111 determines whether or not the sensor signal indicates non-contact with the user.

When it is determined that the user has been separated from the contact sensor 31, the processor 111 deletes the authentication information in the storage area 114b. The processor 111 may delete the authentication information in the storage area 114b when it is determined that the user has been separated from the contact sensor 31 for a predetermined period of time.

Next, an operation example of the authentication system 1' is described.

Since an operation example in which the authentication system 1' registers a template is the same as that in the first embodiment, a description thereof is omitted.

Next, an operation example in which the authentication system 1' stores authentication information is described.

FIG. 11 is a sequence diagram for explaining an operation example in which the authentication system 1' stores authentication information.

Here, assume that the storage area 114a stores a template. Also assume that the storage area 114b does not store authentication information.

First, the user wears the wearable terminal 10' (S41). In this step, the user brings the wearable terminal 10' into the state shown in FIG. 3.

When the user wears the wearable terminal 10', the switch 13 of the wearable terminal 10' is pressed (S42). When the switch 13 is pressed, the processor 111 activates the wearable terminal 10' by using power from the battery 16.

When the wearable terminal 10' is activated, the processor 111 causes the contact sensor 31 to detect contact with the user (S43). The contact sensor 31 transmits a sensor signal to the processor 111 (S44).

Herein, assume that the contact sensor 31 transmits a sensor signal indicating contact with the user to the processor 111.

The processor 111 receives the sensor signal. When the sensor signal is received, the processor 111 causes the fingerprint sensor 17 to acquire fingerprint information (S45). In this step, the user brings their finger into contact with the fingerprint sensor 17. The fingerprint sensor 17 transmits the fingerprint information acquired from the user's finger to the processor 111 (S46).

The processor 111 acquires fingerprint information of the user from the fingerprint sensor 17. When the fingerprint information is acquired, the processor 111 performs fingerprint authentication by comparing the template with the acquired fingerprint information (S47). Here, assume that the processor 111 has succeeded in the fingerprint authentication.

When the fingerprint authentication is performed, the processor 111 stores the authentication information in the storage area 114b (S48).

When the processor 111 stores the authentication information in the storage area 114a, the authentication system 1' ends the operation.

When the contact sensor 31 transmits a sensor signal indicating non-contact with the user, the processor 111 may end the operation. In this case, the processor 111 may wait until the contact sensor 31 transmits a sensor signal indicating contact with the user.

When the processor 111 fails in the fingerprint authentication, the authentication system 1' ends the operation.

Since an operation example in which the authentication system 1' authenticates a user is the same as that according to the first embodiment, description thereof is omitted.

Next, an operation example in which the authentication system 1' deletes the authentication information is described.

Figure 12:
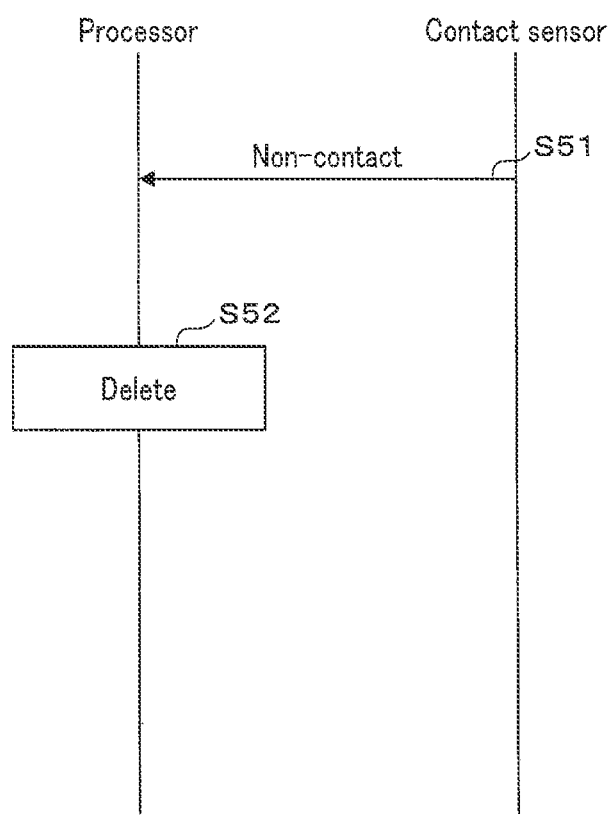
FIG. 12 is a sequence diagram showing an operation example of an authentication system according to the second embodiment.

FIG. 12 is a sequence diagram for explaining an operation example in which the authentication system 1 deletes authentication information.

Here, assume that the storage area 114a stores a template. In addition, assume that the storage area 114b stores authentication information.

Here, assume that the user moves the wrist away from the contact sensor 31.

The contact sensor 31 transmits a sensor signal indicating non-contact with the user to the processor 111 (S51). The processor 111 receives the sensor signal.

When the sensor signal is received, the processor 111 deletes the authentication information in the storage area 114b (S52).

When the processor 111 deletes the authentication information, the authentication system 1 ends the operation.

The processor 111 may turn off the wearable terminal 10' after deleting the authentication information.

The processor 111 may delete the authentication information by the operation of S41 through S44, similarly to the first embodiment.

The contact sensor 31 may transmit a predetermined sensor signal to the processor 111 while being in contact with the user. The contact sensor 31 may not transmit a sensor signal when the contact sensor 31 is separated from the user.

The contact sensor 31 may transmit a predetermined sensor signal to the processor 111 while being away from the user. The contact sensor 31 may not transmit a sensor signal when it comes into contact with the user.

The wearable terminal configured as described above deletes the authentication information when the contact sensor detects that the wearable terminal is separated from the user. As a result, it is possible to more effectively prevent the wearable terminal from being handed over to another person with the wearable terminal holding the authentication information.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the invention. The accompanying claims and their equivalents are intended to cover such forms or modifications as would fall within the scope and spirit of the inventions.

What is claimed is:

1. An authentication device for authenticating a user, the device comprising:
    a biological sensor configured to acquire biological information;
    a storage unit that stores authentication information;
    a communication interface configured to transmit and receive data to and from an external device;
    a detection mechanism configured to detect attachment and detachment of the authentication device; and
    a processor configured to:
        authenticate a user using the biological information acquired by the biological sensor;
        store, when authentication of the user is successful, the authentication information in the storage unit and turn off the authentication device;
        activate the authentication device using power from the communication interface when the communication interface receives a magnetic field from the external device;
        upon receipt of an authentication command through the communication interface, if the storage unit stores the authentication information, transmit an authentication signal indicating that authentication is successful to the external device through the communication interface; and
        when the detection mechanism detects that the authentication device has been removed from the user, delete the authentication information in the storage unit.

2. The authentication device according to claim 1, wherein
    the detection mechanism is a switch that turns on the authentication device, and
    when the switch is pressed and the storage unit does not store the authentication information, the processor authenticates the user using the biological information acquired by the biological sensor, and
    when the switch is pressed and the storage unit stores the authentication information, the processor deletes the authentication information in the storage unit.

3. The authentication device according to claim 2, further comprising:
    a band to be wound around a wrist of the user; and
    a ring-shaped member formed at one end of the band,
    wherein the switch is pressed when the other end of the band passes through the member.

4. The authentication device according to claim 3, wherein
    the switch is installed inside the member.

5. The authentication device according to claim 2, comprising
    a battery that supplies electric power, wherein
    the processor activates the authentication device using the electric power from the battery when the switch is pressed.

6. The authentication device according to claim 1, wherein
    the communication interface supports an NFC connection.

7. The authentication device according claim 1, wherein the biological information is fingerprint information.

8. The authentication device according to claim 3, wherein
the biological sensor is installed inside the band.

* * * * *